(12) United States Patent
Subramaniam et al.

(10) Patent No.: US 9,757,177 B2
(45) Date of Patent: Sep. 12, 2017

(54) DEVICE AND METHODS FOR NERVE MODULATION USING A NOVEL ABLATION CATHETER WITH POLYMERIC ABLATIVE ELEMENTS

(71) Applicant: Boston Scientific Scimed, Inc., Maple Grove, MN (US)

(72) Inventors: Raj Subramaniam, Fremont, CA (US); Zaya Tun, Livermore, CA (US); Daniel J. Horn, Shoreview, MN (US); Derek C. Sutermeister, Eden Prairie, MN (US); James M. Anderson, Fridley, MN (US); Jeffrey S. Lindquist, Maple Grove, MN (US); Kent D. Harrison, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/218,977

(22) Filed: Jul. 25, 2016

(65) Prior Publication Data

US 2016/0331432 A1    Nov. 17, 2016

Related U.S. Application Data

(63) Continuation of application No. 13/711,231, filed on Dec. 11, 2012, now Pat. No. 9,433,760.
(Continued)

(51) Int. Cl.
*A61B 18/00* (2006.01)
*A61M 25/10* (2013.01)
(Continued)

(52) U.S. Cl.
CPC .......... *A61B 18/00* (2013.01); *A61B 18/1492* (2013.01); *A61B 18/18* (2013.01); *A61M 25/10* (2013.01); *A61B 2018/0016* (2013.01); *A61B 2018/0022* (2013.01); *A61B 2018/00077* (2013.01); *A61B 2018/00083* (2013.01);
(Continued)

(58) Field of Classification Search
CPC ................ A61B 18/1492; A61B 18/18; A61B 2018/00136; A61B 2018/0016; A61B 2018/00166; A61B 2018/0022; A61B 2018/00238; A61B 2018/00404; A61B 2018/00434; A61B 2018/00511; A61B 2018/00577; A61B 2018/00791; A61B 2018/1435; A61B 2018/147; A61B 2018/1472; A61B 2218/002; A61M 25/10
See application file for complete search history.

(56) References Cited

U.S. PATENT DOCUMENTS

| | | | | |
|---|---|---|---|---|
| 6,475,213 B1* | 11/2002 | Whayne | ............. | A61B 18/1492 600/374 |
| 2012/0029511 A1* | 2/2012 | Smith | ................ | A61B 18/1492 606/41 |

* cited by examiner

*Primary Examiner* — Amanda Patton

(57) ABSTRACT

The disclosure pertains to an intravascular catheter for nerve modulation, comprising an elongate member having a proximal end and a distal end, a balloon having a lumen and a balloon wall, the balloon wall comprising RF permeable sections and non-electrically conductive sections, an electrode disposed within the balloon and extending distally to the furthest distal RF permeable section. The RF permeable sections may comprise a plurality of RF permeable windows, each window having a greater circumferential dimension than an axial dimension. The intravascular system is suited for modulation of renal nerves.

18 Claims, 15 Drawing Sheets

Related U.S. Application Data

(60) Provisional application No. 61/580,972, filed on Dec. 28, 2011, provisional application No. 61/605,615, filed on Mar. 1, 2012, provisional application No. 61/605,624, filed on Mar. 1, 2012.

(51) Int. Cl.
*A61B 18/18* (2006.01)
*A61B 18/14* (2006.01)

(52) U.S. Cl.
CPC ........... *A61B 2018/00136* (2013.01); *A61B 2018/00166* (2013.01); *A61B 2018/00238* (2013.01); *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/147* (2013.01); *A61B 2018/1435* (2013.01); *A61B 2018/1472* (2013.01); *A61B 2218/002* (2013.01)

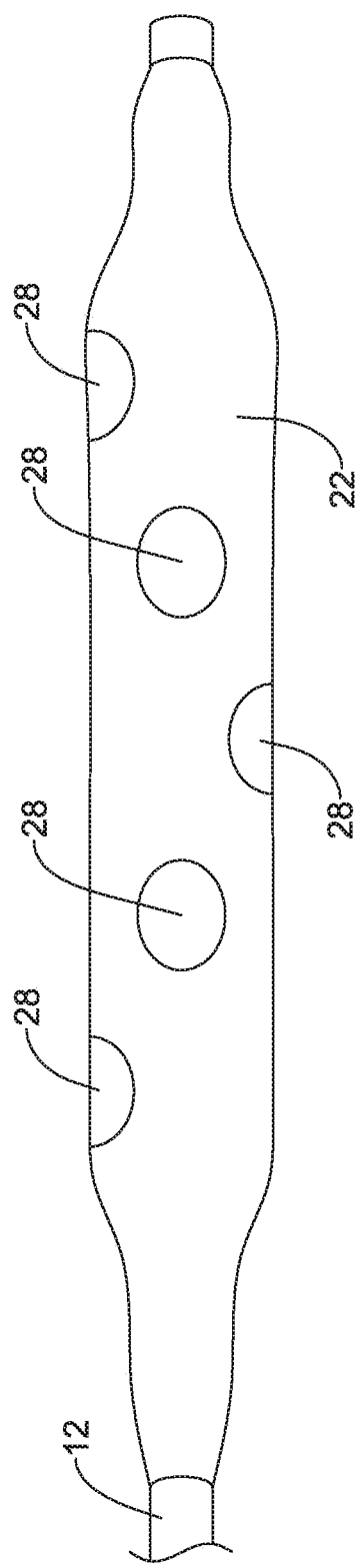

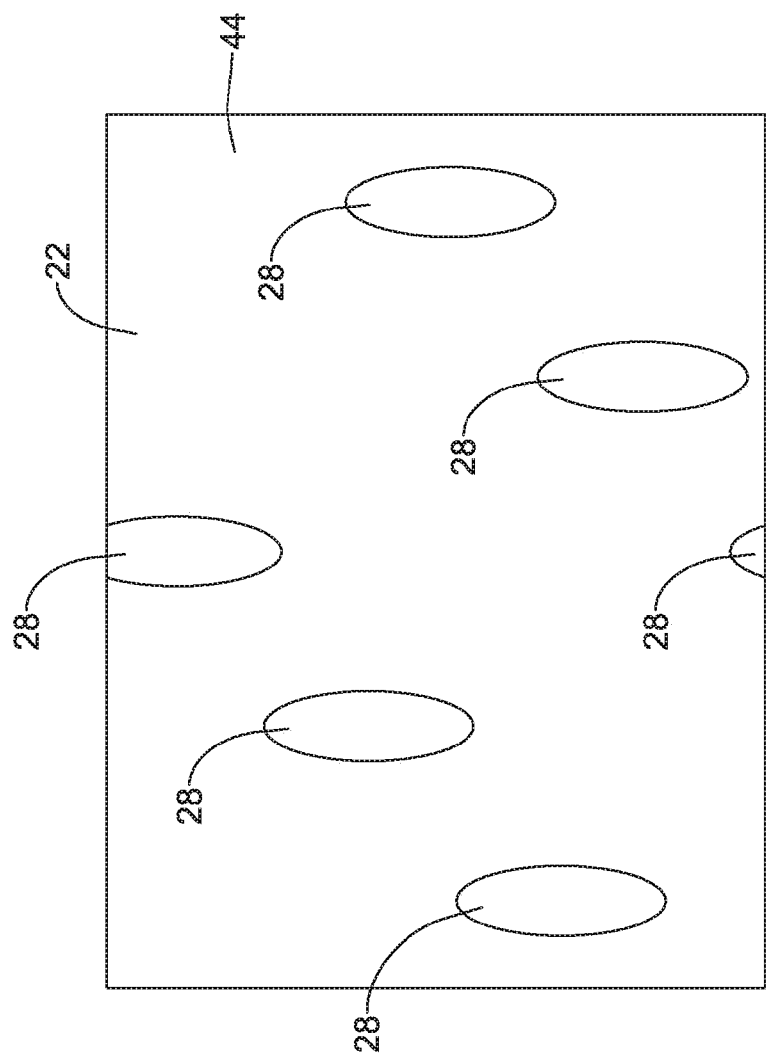

DEVICE AND METHODS FOR NERVE MODULATION USING A NOVEL ABLATION CATHETER WITH POLYMERIC ABLATIVE ELEMENTS

CROSS-REFERENCE TO RELATED APPLICATIONS

This application is a continuation of patent application Ser. No. 13/711,231, filed on Dec. 11, 2012; which claims priority under 35 U.S.C. §119 to U.S. Provisional Application Ser. No. 61/580,972, filed Dec. 28, 2011; to U.S. Provisional Application Ser. No. 61/605,615, filed Mar. 1, 2012; and to U.S. Provisional Application Ser. No. 61/605,624, filed Mar. 1, 2012, all of which are herein incorporated by reference.

FIELD

The invention generally pertains to percutaneous and intravascular devices for nerve modulation and/or ablation.

BACKGROUND

Certain treatments require the temporary or permanent interruption or modification of select nerve function. One example treatment is renal nerve ablation which is sometimes used to treat conditions related to congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many body tissues such as nerves, including renal nerves, brain tissue, cardiac tissue and the tissue of other body organs are in close proximity to blood vessels or other body cavities and thus can be accessed percutaneously or intravascularly through the walls of the blood vessels. In some instances, it may be desirable to ablate perivascular nerves using a radio frequency (RF) electrode. In other instances, the perivascular nerves may be ablated by other means including application of thermal, ultrasonic, laser, microwave, and other related energy sources to the vessel wall.

In treatments involving perivascular nerves such as renal nerves, treatment methods employing such energy sources have tended to apply the energy as a generally circumferential ring to ensure that the nerves are modulated. However, such a treatment, may result in thermal injury to the vessel wall near the electrode and other undesirable side effects such as, but not limited to, blood damage, clotting, weakened vessel wall, and/or protein fouling of the electrode.

SUMMARY

It is therefore desirable to provide for alternative systems and methods for tissue treatment such as intravascular nerve modulation treatments that distribute ablation, or modulations sites along and around the vessel or other body cavity.

Some embodiments of the invention are directed to a balloon catheter configured for tissue modulation such as nerve modulation and/or ablation. The balloon catheter includes an inflatable balloon at or proximate a distal end of the device. The wall of the balloon is constructed so as to allow electricity such as RF energy through at certain locations and to prevent the transmission of RF energy or electricity at other locations. An electrode extends through the lumen of the balloon to supply the electricity or RF energy. In use, the balloon is inflated with a conductive fluid such as saline and positioned at a desired location for treatment. In some embodiments, the balloon may be in circumferential contact with a wall such as a blood vessel wall at the treatment location. The electrode is activated and the RF energy is transmitted through the conductive fluid and out the balloon through the RF permeable locations to modulate or ablate tissue.

The balloon may be a multilayer balloon with a first layer made from an RF permeable material and a second layer made from an electrically insulative material. The RF permeable material may be, for example, a hydrophilic polyurethane, and the electrically insulative material may be, for example, a (non-hydrophilic) polyurethane. The locations or windows that allow the transmission of RF energy do not include the electrically insulative material. These balloon walls of these RF permeable materials may be formed of a single layer of the RF permeable material and the remainder of the balloon may have two layers, one of the RF permeable material and one of the electrically insulative material.

The balloon catheter may include other elements such a multi-lumen catheter shaft. The multi-lumen catheter shaft may include a guide wire lumen and one or two fluid lumens as well as conductive members to connect the electrode and one or more sensors to a power and control system. For embodiments that include two fluid lumens, one fluid lumen may be used to introduce the conductive fluid into the balloon and the other fluid lumen may be used to evacuate the conductive fluid from the balloon, in this manner, the conductive fluid may be circulated within the balloon. In some embodiments, the fluid intake lumen has a fluid inlet fluidly connected to the balloon lumen at a distal location in the balloon and the fluid outlet lumen has a fluid outlet fluidly connected to the balloon lumen at a more proximal location in the balloon.

The electrode may be any suitable electrode member and may, for example, be a ribbon electrode that is helically wound about the catheter shaft within the balloon lumen and may be made from any suitable material such as platinum.

One illustrative embodiment has a balloon with three, four or more RF permeable windows through the balloon wall. The windows may be circular, oval, diamond-shaped, bowtie-shaped, or another appropriate shape and are spaced out longitudinally and circumferentially. Preferably, the windows are arranged so that the treatment area receives a tissue modulation or ablation treatment provides the desired coverage. For example, in some embodiments, the windows are arranged so that any line drawn longitudinally along the balloon wall passes through at least one window. Such a window arrangement allows for coverage around the circumference of the blood vessel while still permitting the windows to be spaced apart longitudinally. In other embodiments, one or more of the windows are arranged so that a line drawn longitudinally along the balloon wall passes through pans of two windows. In other embodiments, the number and arrangement of windows is such that so that any line drawn longitudinally along the balloon wall passes through at least two windows Another illustrative embodiment includes one or more helically shaped windows along the length, or along a portion of the length of the balloon. Another illustrative embodiment includes one or more windows that extend circumferentially around the balloon.

Another illustrative embodiment includes a helically shaped balloon where the balloon lumen is helically shaped and wraps around the catheter shaft. In this embodiment, one or more windows may be positioned on the outer diameter of the balloon catheter and are arranged so that any line drawn longitudinally (i.e. parallel to the catheter shaft) along the outer diameter of the balloon wall passes through at least one window. In one illustrative embodiment, a helically shaped window extends along the outer diameter of the helically shaped balloon.

In another illustrative embodiment, the RF permeable portions of the balloon are more compliant than the electrically insulative portions and pressure provided by the conductive fluid may cause the windows to bulge out. Such variations in the relative compliance of the different portions of the balloon may be effected by material selection, durometer selection, by varying the thickness of the layers or portions of layers or by other suitable method.

In another illustrative embodiment, the windows are molded to extend out from the balloon wall beyond the electrically insulative material.

In one illustrative method of use, a balloon catheter according to an embodiment of the invention is inserted percutaneously and/or intravascularly to a treatment location using a guidewire, a guide catheter or other conventional means. The balloon is inflated with the conductive fluid and the conductive fluid is circulated within the balloon. The electrode is activated and RF energy is transmitted from the electrode and through the conductive fluid and RF permeable windows into the tissue of the desired treatment area. The treatment may be ended after a predetermined time or after a predetermined condition is met. For example, impedance may be measured through the electrode and the treatment may be ended after a predetermined change in the measured impedance.

The above summary of some example embodiments is not intended to describe each disclosed embodiment or every implementation of the invention.

BRIEF DESCRIPTION OF DRAWINGS

The invention may be more completely understood in consideration of the following detailed description of various embodiments in connection with the accompanying drawings, in which:

FIG. 10a is a schematic view of a renal nerve modulation system.

FIG. 10b is a schematic view of the renal nerve modulation system of FIG. 10a.

FIGS. 11a-11d are projection views of the outer surface of example balloons of renal nerve modulation systems.

Figure 1:
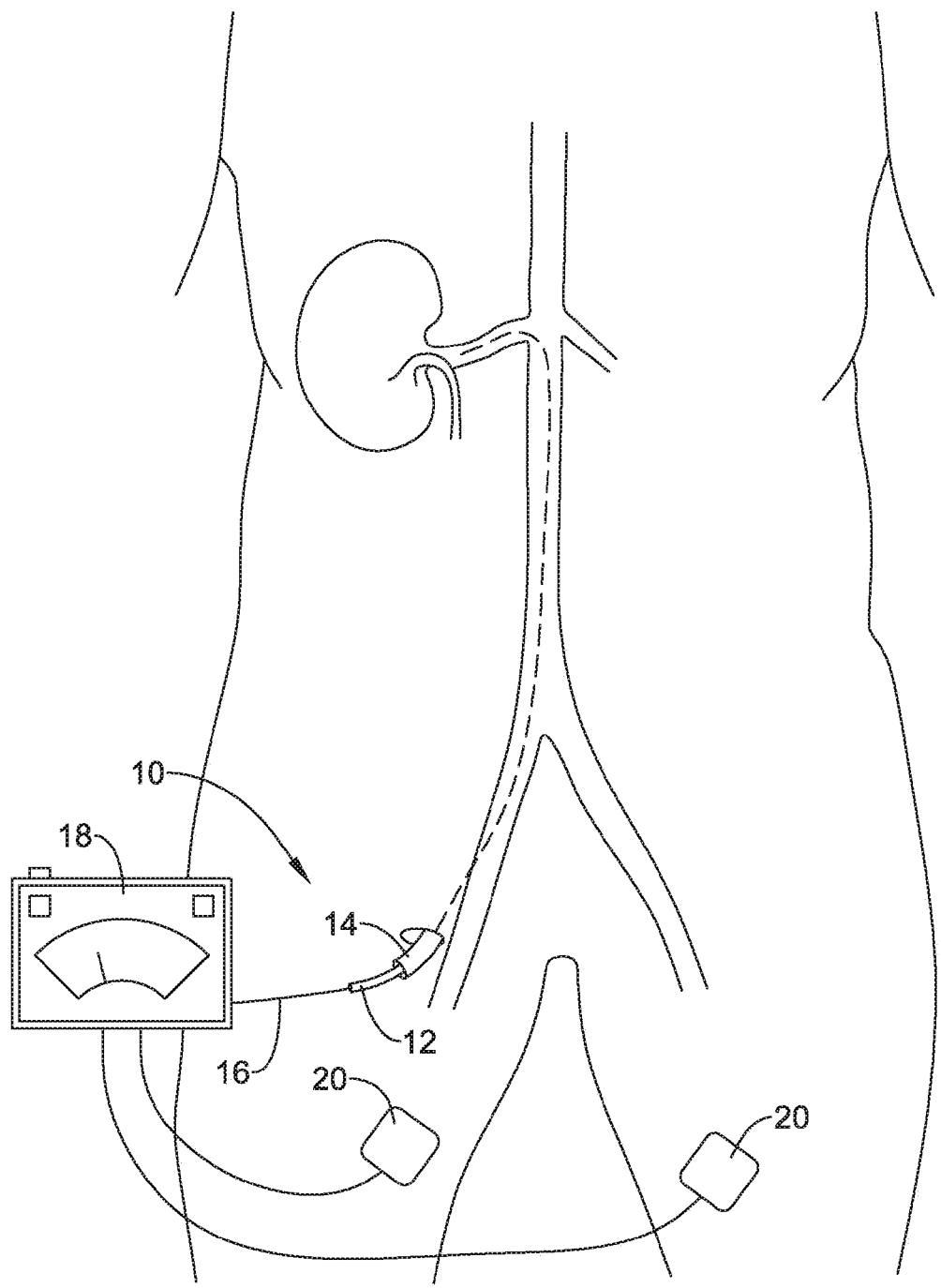
FIG. 1 is a schematic view illustrating a renal nerve modulation system in situ.

While the invention is amenable to various modifications and alternative forms, specifics thereof have been shown by way of example in the drawings and will be described in detail, it should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments" etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described unless cleared stated to the contrary.

While the devices and methods described herein are discussed relative to renal nerve modulation through a blood vessel wall, it is contemplated that the devices and methods may be used in other applications where nerve modulation and/or ablation are desired. The term modulation refers to ablation and other techniques that may alter the function of affected nerves and other tissue such as brain tissue or cardiac tissue. When multiple ablations are desirable, they may be performed sequentially by a single ablation device.

FIG. 1 is a schematic view of an illustrative renal nerve modulation system in situ. System 10 may include one or more conductive element(s) 16 for providing power to a renal ablation system including a renal nerve modulation device 12 disposed within a delivery sheath 14, which may be adapted to slidably contain the renal nerve modulation device 12 when the radially expanding region (not shown) of the elongate member is in a non-expanded configuration, the details of which can be better seen in subsequent figures. A proximal end of conductive elements) 16 may be connected to a control and power element 18, which supplies necessary electrical energy to activate one or more electrodes to which the distal end of wire(s) 16 are attached at or near a distal end of the renal nerve modulation device 12. When suitably activated, the electrodes are capable of ablating tissue as described below. The terms electrode and electrodes may be considered to be equivalent to elements capable of ablating adjacent tissue in the disclosure which follows. Suitable materials for the delivery sheath 14, elongate member 12 and elements capable of ablating adjacent tissue are known in the art and in some embodiments may include internal and/or external layers of lubricious material(s). In some instances, return electrode patches 20 may be supplied on the legs or at another conventional location on the patient's body to complete the circuit. A proximal hub (not illustrated) having ports for a guide wire, an inflation lumen and a return lumen may also be included.

The control and power element 18 may include monitoring elements to monitor parameters such as power, temperature, voltage, pulse size, impedance and/or shape and other suitable parameters, with sensors mounted along renal nerve modulation device 12, as well as suitable controls for performing the desired procedure. In some embodiments, the power element 18 may control a radio frequency (RF) electrode. The electrode may be configured to operate at a frequency of approximately 460 kHz. It is contemplated that any desired frequency in the RF range may be used, for example, from 450-500 kHz. It is further contemplated that other ablation devices may be used as desired, for example, but not limited to resistance heating, ultrasound, microwave, and laser devices and these devices may require that power be supplied by the power element 18 in a different form.

Figure 2:
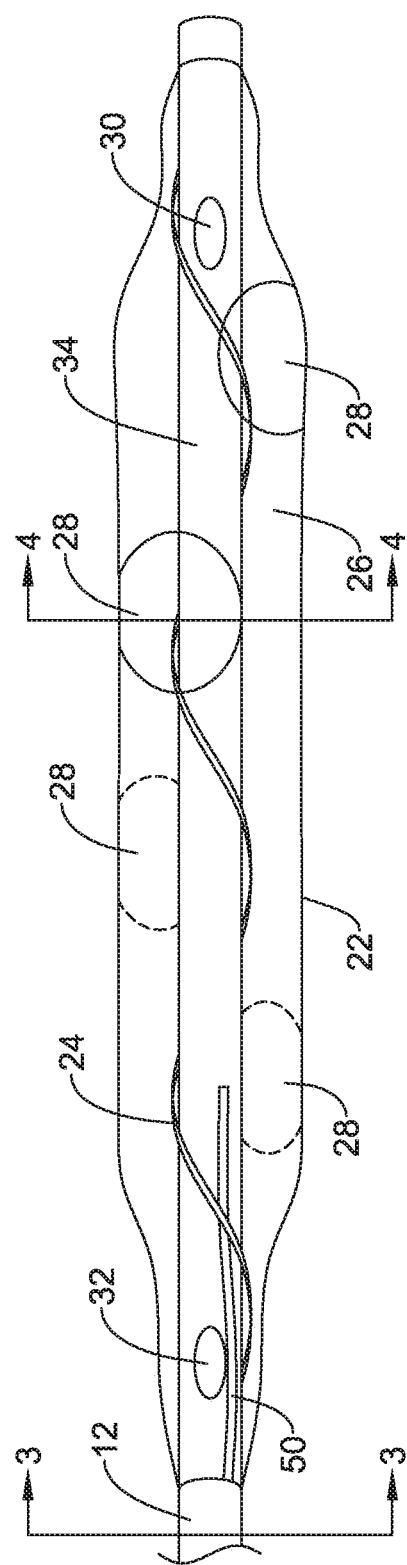
FIG. 2 is a schematic view illustrating the distal end of a renal nerve modulation system.

FIG. 2 illustrates the distal portion of a renal nerve modulation device 12. Renal nerve modulation device 12 includes a balloon 22 and an electrode 24. When in use, the balloon is preferably filled with a conductive fluid 26 such as saline to allow the ablation energy to be transmitted from the electrode 24 through windows 28 that are permeable to RF radiation. Other appropriate conductive fluids include hypertonic solutions, contrast solution and mixtures of saline or hypertonic saline solutions with contrast solutions. The conductive fluid may be introduced through a fluid inlet 30 and evacuated through a fluid outlet 32, both in a central shaft 34. One or more sensors 50, such as thermocouple, may be included and may be disposed on the shaft 34, on the balloon 22 or at another suitable location.

Figure 3:
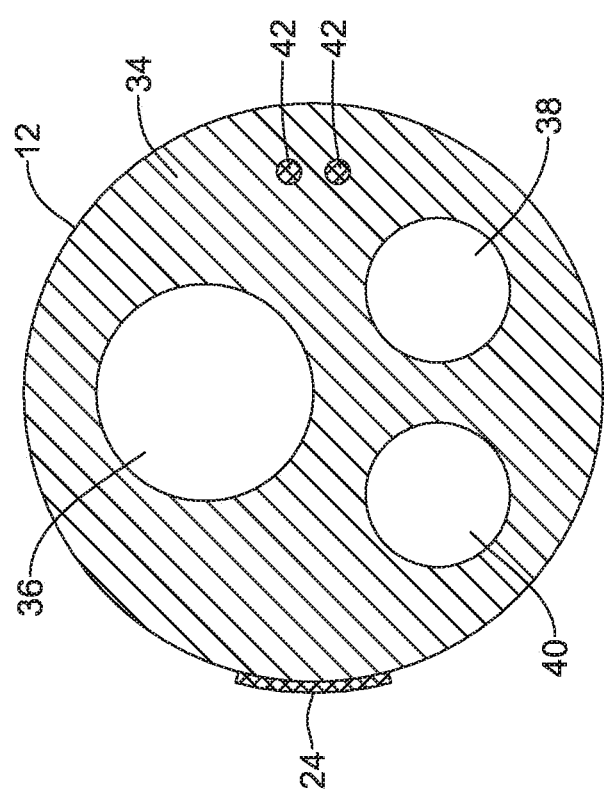
FIG. 3 is a cross-sectional view of the renal, nerve modulation system of FIG. 2.

A cross-sectional view of the shaft 34 of the renal nerve modulation device 12 proximal to the balloon is illustrated in FIG. 3. Shaft 34 may include a guidewire lumen 36, a lumen 38 connected to the fluid outlet 30, and a lumen 40 connected to the fluid inlet 32. The electrode 24, or a conductive element to supply power to the electrode may extend along the outer surface of the shaft or may be embedded within the shaft. The electrode 24 proximal to the balloon is preferably electrically insulated and is used to transmit power to the portion of the electrode disposed in the balloon. Conductors 42, two of which are illustrated in FIG. 3, may be used to supply power and to allow information to return from the one or more sensors 50. In some embodiments, the guidewire lumen and/or one of the fluid lumens 38, 40 may be omitted. In some embodiments, the guidewire lumen extends from the distal end of the device to a proximal hub. In other embodiments, the guidewire lumen can have a proximal opening that is distal the proximal portion of the system. In some embodiments, the fluid lumens 38, 40 can be connected to a system to circulate the fluid through the balloon 22 or to a system that supplies new fluid and collects the evacuated fluid. It can be appreciated that embodiments may function with merely a single fluid inlet lumen and a single fluid outlet into the balloon. It can also be appreciated that other lumen configurations are contemplated. For example, the three lumens may be disposed within each other or may be concentric. The guidewire lumen may be the innermost lumen and may be surrounded by the fluid inlet lumen which, in turn may be surrounded by the fluid outlet lumen. In another contemplated embodiment, only one of the fluid inlet and fluid outlet lumens is disposed around the guidewire lumen and the other of the fluid inlet and fluid outlet lumens extends parallel to and spaced apart from the guidewire lumen. Another contemplated embodiment lacks the fluid outlet lumen and the fluid inlet lumen is disposed around or concentrically around the guidewire lumen. In another contemplated embodiment, the guidewire lumen is omitted and the system includes only the fluid inlet lumen or only the fluid inlet and outlet lumens.

Figure 4:
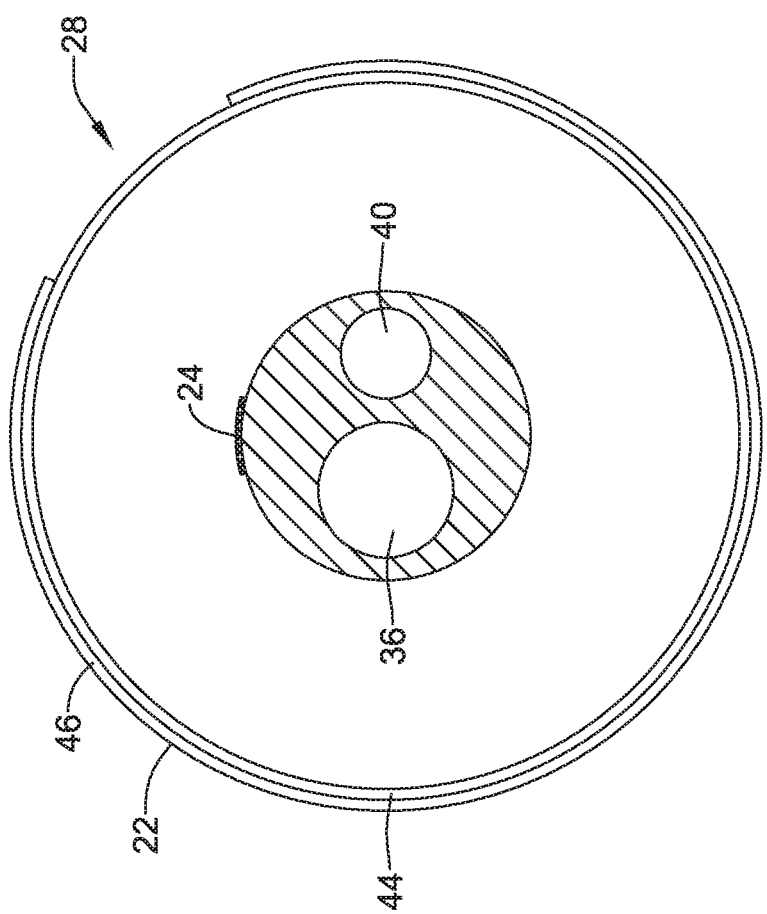
FIG. 4 is another cross-sectional view of the renal nerve modulation system of FIG. 2.

A cross-sectional view of the shaft 34 distal to fluid outlet 32 is illustrated in FIG. 4. The guidewire lumen 36 and the fluid inlet lumen 36 are present, as well as electrode 24. In the presently illustrated embodiment, conductors 42, which are connected to one or more sensors 50, are not present in this cross-sectional view. It can be appreciated that in embodiments that have one or more distal sensors, one or more conductors 42 may be present, to connect with then.

Balloon 22 is shown in cross-section as having a first layer 44 and a second layer 46. A window 28 is formed in balloon 22 by the absence of second layer 46. First layer 44 is preferably made from an RF permeable material. One suitable material is a hydrophilic polyurethane. Other suitable materials include other hydrophilic polymers such as hydrophilic Pebax, hydrophilic nylons, hydrophilic polyesters, or block co-polymers with built-in hydrophilic blocks. Hydrophilic Pebax grades that may be suitable include Pebax MV1074, Pebax MV 1041, Pebax MP 1878, Pebax MV-3000, and Pebax MH-1657. In some embodiments, one ore more of the hydrophilic polymers such as the hydrophilic Pebax grades are used in blends with other polymers used in balloons such as Pebax 6333, Pebax 7033, Pebax 7233, Nylon 12, Vestamid L2101F, Grilamid L20, and Grilamid 125. Suitable hydrophilic polymers may exhibit between 6% to 120% hydrophilicity (or % water absorption), between 20% to 50% hydrophilicity or other suitable range. The second layer 46 is preferably made from an electrically non-conductive polymer such as a non-hydrophilic polyurethane, Pebax, nylon, polyester or block-copolymer. Other suitable materials include any of a range of electrically non-conductive polymers. The materials of the first layer and the second layer may be selected to have good bonding characteristics between the two layers. For example, a balloon 22 may be formed from a first layer 44 made from a hydrophilic Pebax and a second layer 46 made from a regular or non-hydrophilic Pebax. In other embodiments, a suitable tie layer (not illustrated) may be provided between the two layers.

Figure 5:
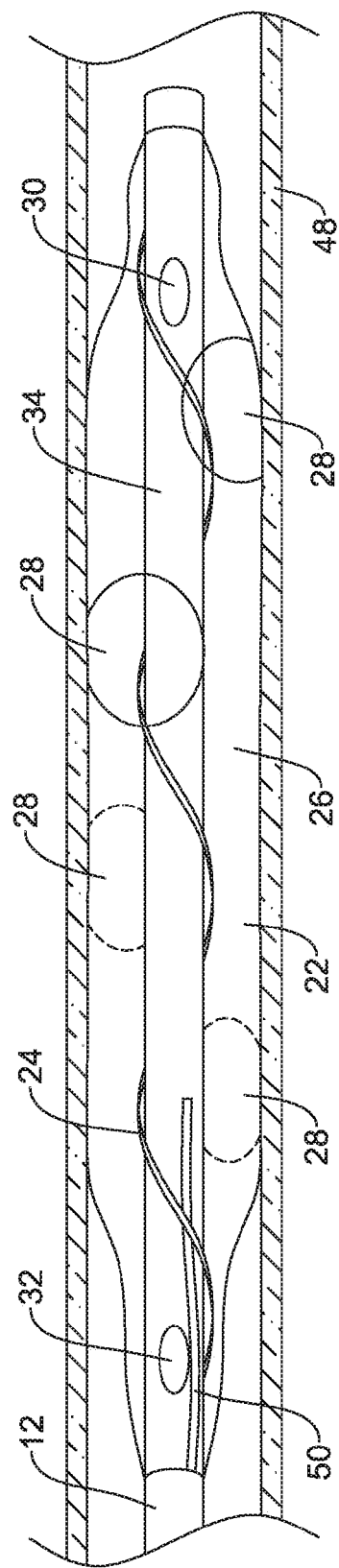
FIG. 5 is a schematic view illustrating the renal nerve modulation system of FIG. 2 in situ.

FIG. 5 illustrates the distal end of device 12 in situ. Preferably, the device 12 is available in various sizes, and a size is selected that will allow the windows 28 of the balloon 22 to contact the wall of a blood vessel 48. The balloon is preferably somewhat compliant so that a balloon having a nominal 4 mm diameter can be expanded to fit a blood vessel of between 3.5 mm and 5 mm.

The particular balloon illustrated in FIG. 5 may be suitable for use in a renal nerve modulation application. Renal nerve extends generally longitudinally around the outside of a renal artery. This means that one can vary the longitudinal position of any particular circumferential treatment and achieve the same nerve modulation effect. Thus windows 28 are arranged to achieve complete circumferential coverage of the blood vessel while spaced apart longitudinally. In this particular case, the four windows 28 each cover a different 90 degree are of the blood vessel. Each window may cover more than a 90 degree are. For example, the windows 28 may cover a 100 or 110 degree are to allow for some overlapping coverage of the windows 28. Windows 28 of this embodiment are four in number and generally circular in shape. It can be appreciated that, variations in the number of windows and the shape of the windows are contemplated. For example, embodiments are contemplated which include 1, 2, 3, 4, 5, 6, 7, 8, 9, 10 or more windows and which include windows that are circular, oval, rectangular, or polygonal. Moreover, the windows having a different length and width may be oriented so that the largest dimension is parallel to the longitudinal axis, perpendicular to the longitudinal axis or at another angle with respect to the longitudinal axis such as a 45 degree angle. In some embodiments, each window may have an aspect ratio of 2:1, 3:1 or 4:1, where the major dimension is perpendicular to the longitudinal axis of the balloon. In some embodiments, the window or windows may have a custom pattern to provide a particular treatment pattern.

Electrode 24 may be a flat ribbon electrode made from platinum, gold, stainless steel, cobalt alloys, or other non-oxidizing materials. In some instances, titanium, tantalum, or tungsten may be used. Electrode 24 may extend along substantially the whole length of the balloon 22 or may extend only as far as the distal edge of the most distal window 28. The electrode 24 may have a generally helical shape and may be wrapped around shaft 34. In some cases, electrode 24 may be bonded to shaft 34. The electrode 24 and windows 28 may be arranged so that the electrode extends directly under the windows 28. In some embodiments, electrode 24 may be a wire or may be a tubular member disposed around shaft 34. In some embodiments, a plurality of electrodes 24 may be used and each of the plurality may be fixed to the shaft 34 under windows 28 and may share a common connected to conductive element 16. In other embodiments that include more than one electrode, each electrode may be separately controllable. In such embodiments, the balloon may be partitioned into more than one chamber and each chamber may include one or more electrodes. The electrode may be selected to provide a particular level of flexibility to the balloon to enhance the maneuverability of the system. It can be appreciated that there are many variations contemplated for electrode 24.

Figure 6:
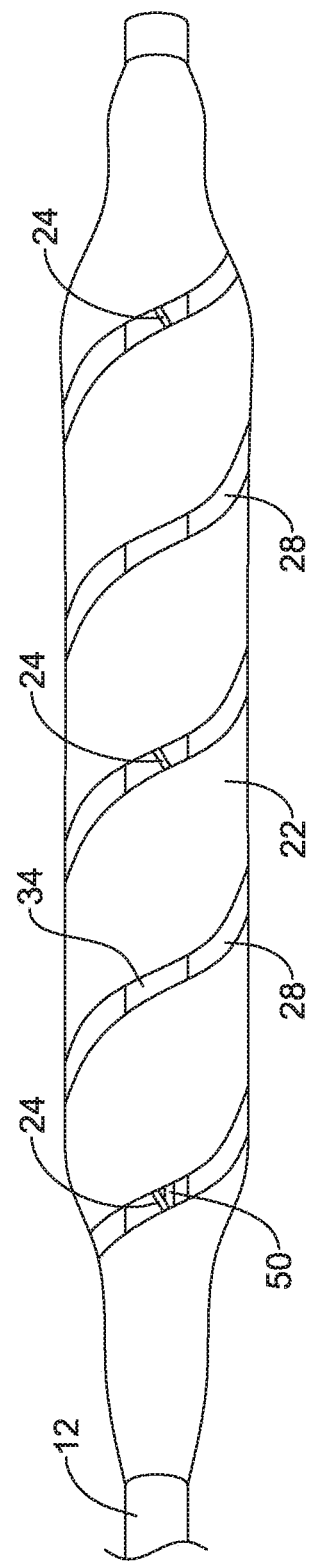
FIG. 6 is a schematic view of a renal nerve modulation system.

FIG. 6 illustrates the distal port ion of another renal nerve modulation device 12 that is similar to the device 12 of FIG. 2 except as described herein. The renal nerve modulation device 12 of FIG. 6 includes previously described elements such as the shaft 34, the multi-layer balloon 22 and the electrode 24. Rather than a plurality of windows 28 as illustrated in the FIG. 2 embodiment, this embodiment has a single helical window 28. Helical window 28 may wrap around the balloon 22 for at least one full turn, or for 2, 3, 4, 5 or more turns as illustrated. Some embodiments include two or more helical, windows 28 spaced apart from each other and winding around the balloon 22 at the same pitch.

Figure 7:
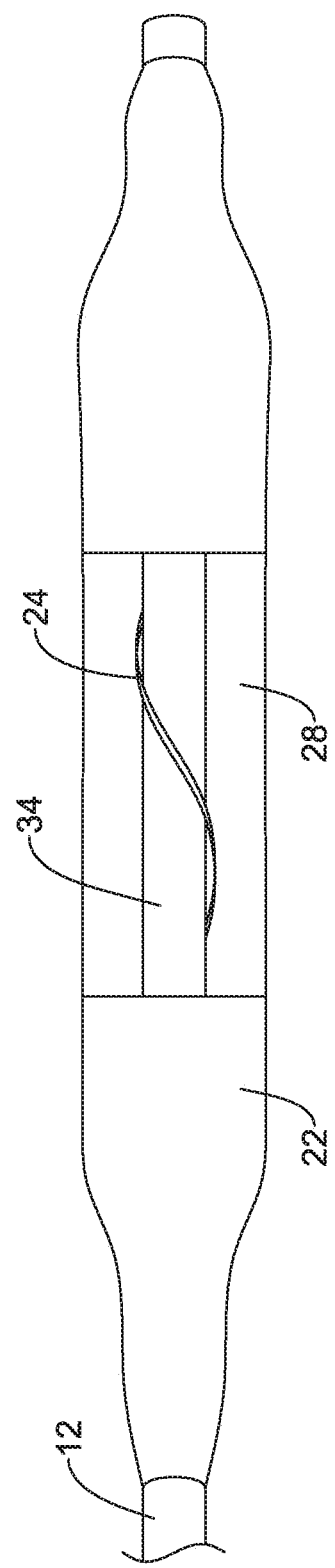
FIG. 7 is a schematic view of a renal nerve modulation system.

Another variation is illustrated in FIG. 7, in which, rather than the plurality of balloons 28 illustrated in the FIG. 2 embodiment, this embodiment has a single balloon 38 that extends circumferentially around the middle portion of balloon 22. Two, three or more like windows 28 may be included in other contemplated variations of this embodiment. In one contemplated variation, the entire balloon wall is permeable to RF energy. Such an embodiment may have a balloon that, includes a layer 44 and does not have a layer 46.

Figure 8:
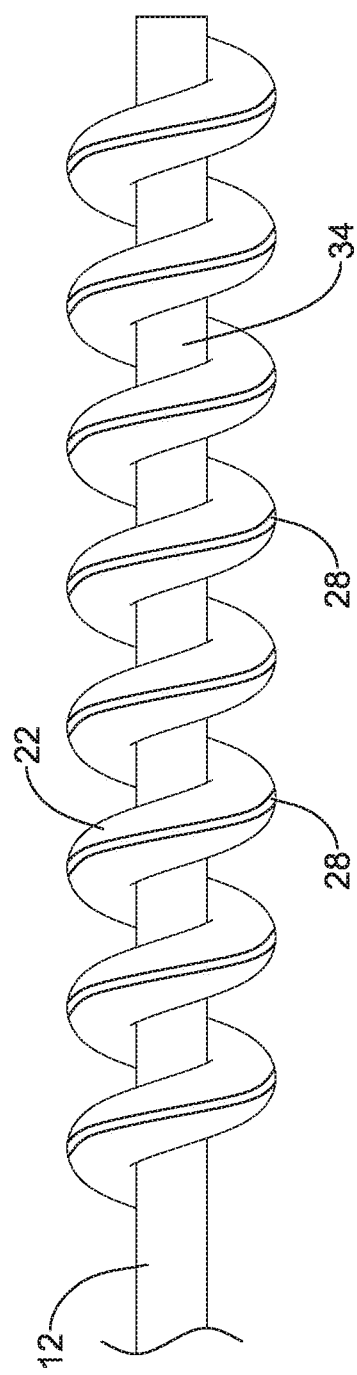
FIG. 8 is a schematic view of a renal nerve modulation system.
Figure 9:
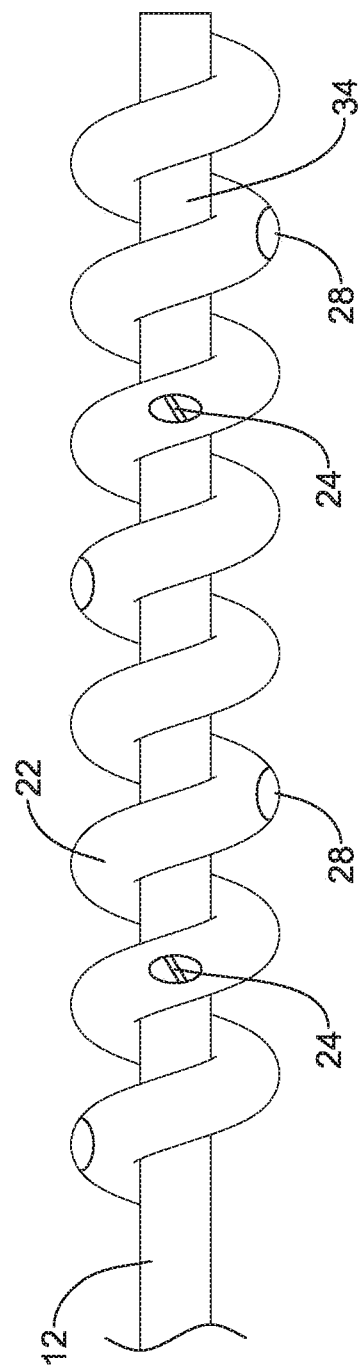
FIG. 9 is a schematic view of a renal nerve modulation system.

FIG. 8 illustrates the distal portion of another renal nerve modulation device 12 that is similar to the device 12 of FIG. 2 except as described herein. The renal nerve modulation device 12 of FIG. 7 includes previously described elements such as the shaft 34, the multi-layer balloon 22 and the electrode 24 (not illustrated). Balloon 22 of this embodiment is helically shaped and is wrapped around shaft 34. A window 28 is helically shaped and follows the outer diameter of the spiral. A variation of this embodiment is illustrated in FIG. 9 in which windows 28 are disposed periodically along the outer diameter of the spiral balloon 22. The windows are preferably arranged to provide complete circumferential coverage while being spaced longitudinally. The number and shape of the windows 28 may be varied as desired.

Figure 10B:
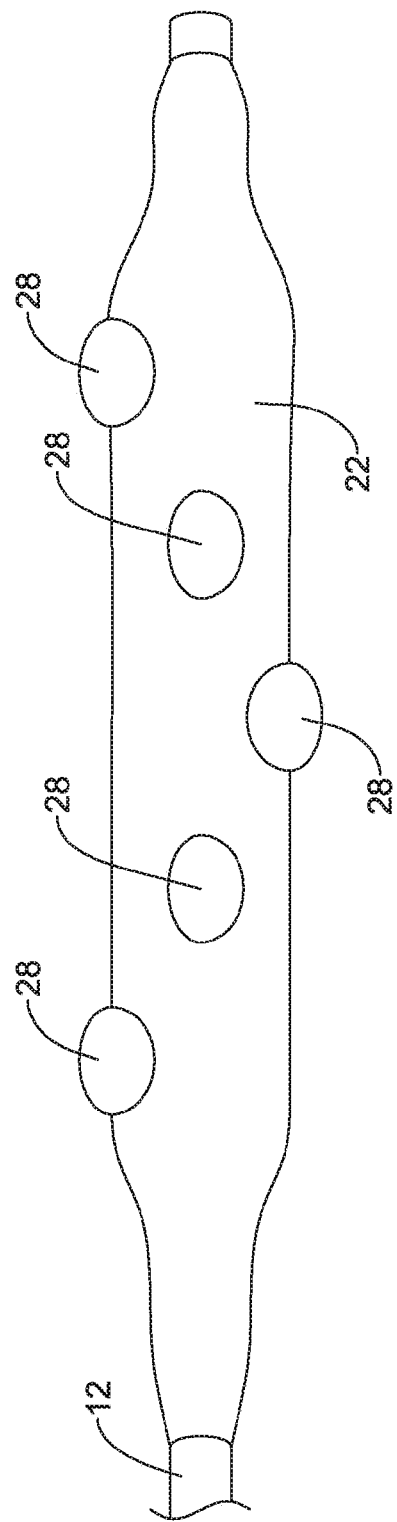

FIGS. 10a and 10b illustrate the distal portion of another renal nerve modulation device 12 that is similar to the device 12 of FIG. 2 except as described herein. FIG. 10a illustrates the device 12 expanded with nominal pressure and FIG. 10b illustrates the device 12 expanded with higher pressure. The higher pressure allows the windows 28 to expand out beyond the outer surface of the second layer 46 of the balloon. In this manner, a particular size of device 12 of FIGS. 10a and 10b may be suitable for use with a wider range of sizes of blood vessels. Device 12 may be made in a variety of ways. It can be appreciated, with reference to FIG. 4, the windows 28 may be thinner than the other portions of balloon 22. A thinner layer of a compliant polymer such as the hydrophilic polyurethane may be more readily expanded than the double layer of material present in the rest of the balloon. This effect may be enhanced by using a less compliant material for the second layer 46 of the balloon 22 or by increasing the thickness of the second layer 46. Suitable materials may include a less-compliant polyurethane (different durometers 85A to 55D), a nylon or a polyethylene terephthalate (PET) or any suitable electrically non-conductive polymer.

In a variation of the embodiment of FIG. 10b, the balloon may be molded or heat-treated so that windows 28 are shaped to be concave as illustrated in this figure under nominal pressure. In such an embodiment, the windows may contact the vessel wall under lower pressure and the balloon would be expandable to different diameters by the application of different amounts of pressure.

FIGS. 11a-11d illustrate projections of the cylindrical central portion of a balloon wall (i.e. the figure illustrates the cylindrical central portion of the balloon wall as if it were cut open and laid flat). The balloon wall of these figures may be readily incorporated into any of the nerve modulation systems described herein. Balloon 22 includes a plurality of windows 28 defined by an absence of electrically insulative layer 44. The windows are arranged on the balloon such that their greatest dimension extends circumferentially (i.e. along a circumference of the cylindrical balloon wall) and their narrowest dimension extends axially (i.e. in the direction of the central longitudinal axis of the balloon 22). The windows 28 are arranged such that any line drawn from the proximal end of the cylindrical balloon wall to the distal end of the cylindrical balloon wall passes through at least one balloon.

The windows may overlap circumferentially while being spaced apart axially. If a line drawn from the proximal end of the cylindrical balloon wall to the distal end of the cylindrical balloon wall passes through two balloons, those two balloons are said to circumferentially over lap.

The degree of circumferential overlap may be expressed in terms of the circumferential dimension of a window 28, in terms of the circumference of the balloon or in terms of an absolute dimension. For example, two adjacent windows may exhibit circumferential overlap that is between 0.2 and 0.8 mm, that is between 0.3 and 0.7 mm, that is between 0.4 and 0.6 mm, that is at least 0.3 mm, that is at least 0.4 mm, or that is at least 0.5 mm, or that is between 20% and 30% of the circumferential dimension of one of the two windows, that is between 24% and 26% of the circumferential dimension of one of the two windows, that is between 5% and 15% of a circumferential dimension of the cylindrical balloon wall, that is between 6% and 7% of a circumferential dimension of the cylindrical balloon wall, or that is between 10% and 14% of a circumferential dimension of the cylindrical balloon wall, for example.

The windows 28 preferably have a greater circumferential dimension than axial dimension. For example, the ratio of axial dimension to circumferential dimension for a window may be greater than 1.5:1, greater than 2:1, greater than 3 to 1 or some other suitable number. A window may have an axial dimension of 1 mm, 1.25 mm, 1.5 mm, 1.75 mm, 2 mm, 2.25 mm, 2.5 mm or other suitable dimension and a circumferential dimension of greater than 3 mm such as 3 mm, 3.5 mm, 4 mm, 4.5 mm or 5 mm. The circumferential dimension of a window 28 may be 20%, 25%, 30% or other suitable percentage of the circumferences of the cylindrical portion of the balloon wall.

Figure 11A:
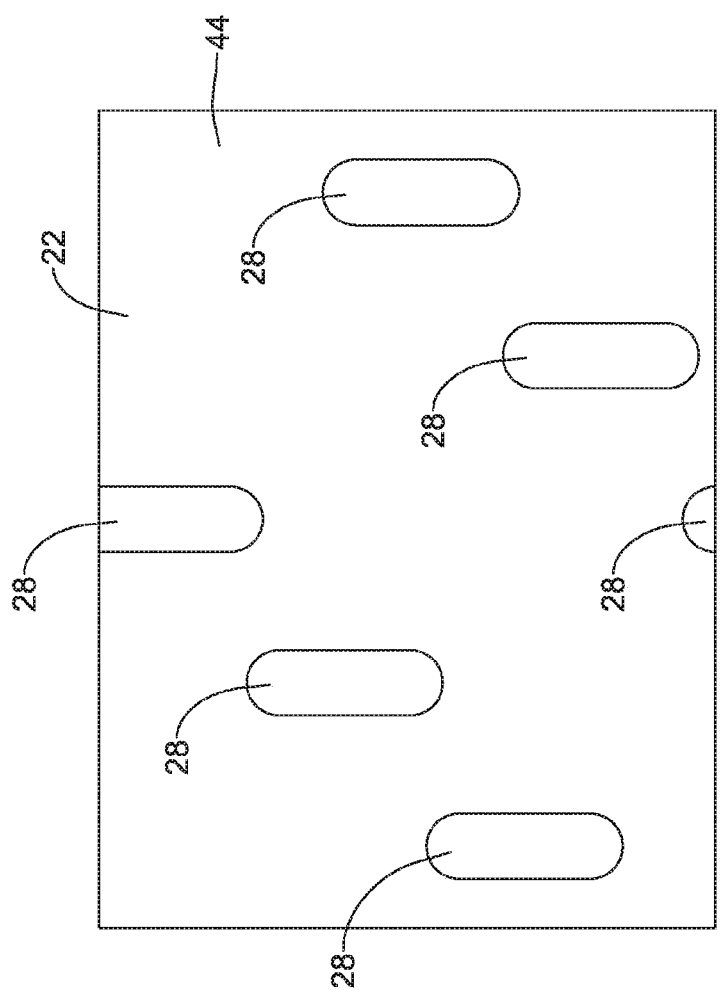

The windows 28 of FIGS. 11a and 11b are shown as being arranged in a generally helical manner in that each adjacent window is offset axially and circumferentially (while overlapping circumferentially) from the previous window. Any number of windows sufficient to provide complete circumferential coverage may be used. In the embodiment of FIG. 11a, five windows 28 are illustrated. Some embodiments may be include 3, 4, 5, 6, 7, 8, 9, 10 or more windows and, if arranged helically as illustrated in FIG. 6, may extend for more than one turn around the balloon wall. It will be appreciated that a helical configuration is not necessary to provide complete circumferential coverage. Complete circumferential coverage means that the windows are arranged such that any line drawn from the proximal end of the cylindrical balloon wall to the distal end of the cylindrical balloon wall passes through at least one balloon.

Figure 11C:
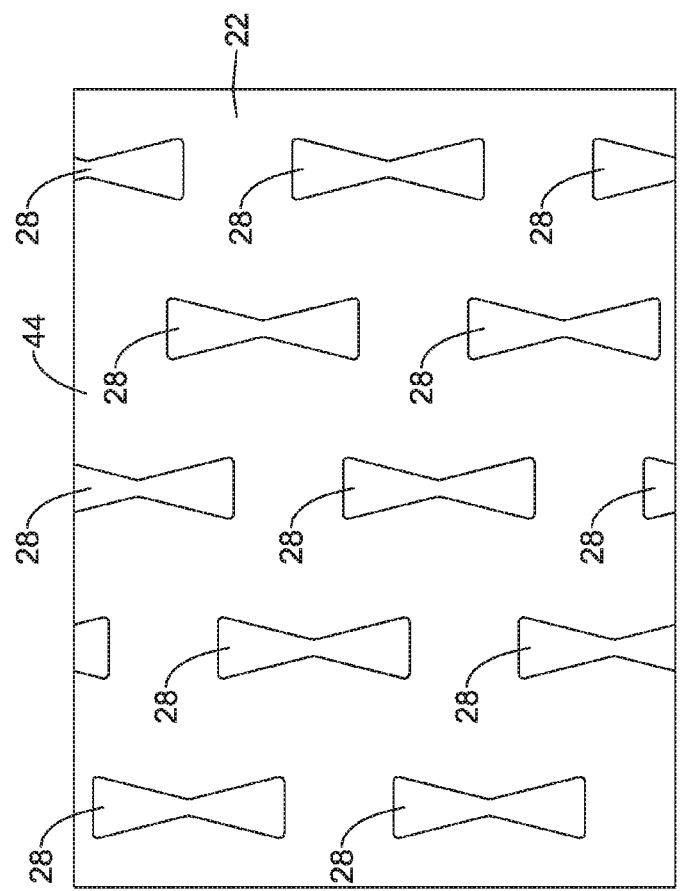
Figure 11D:
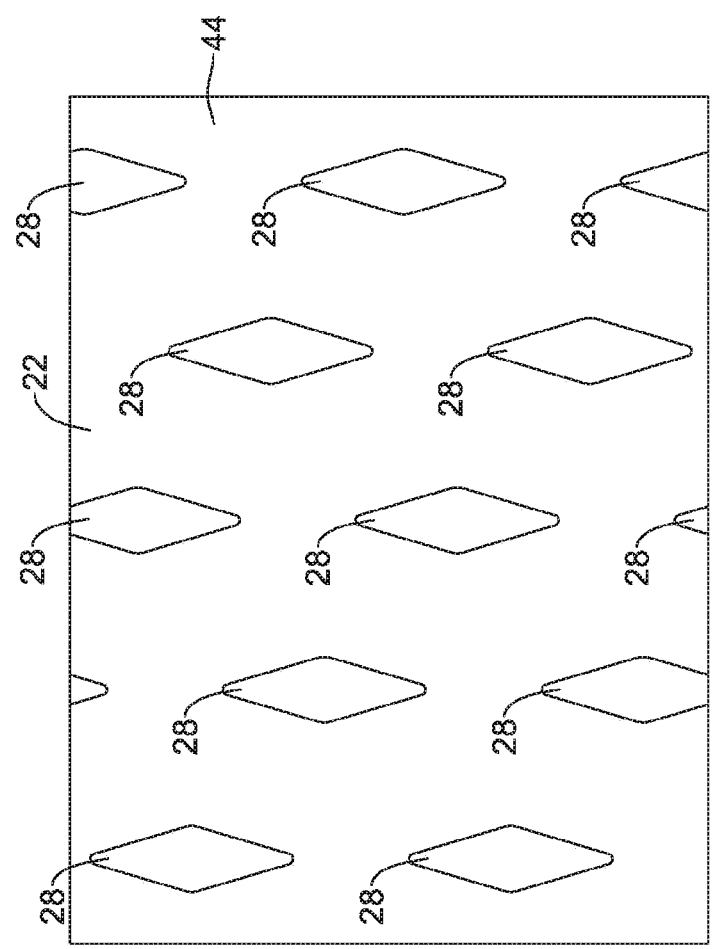

The windows of FIG. 11a are illustrated as oblong. FIGS. 11b-11d illustrate other suitable window shapes such as oval (FIG. 11b), bowtie (FIG. 11c) and diamond (FIG. 11d).

FIGS. 11c and 11d illustrate balloon patterns where more than one window 28 located, along the same circumference such that windows are in a grid pattern. The windows may be thought to be located on each of the intersections of an imaginary grid where the lines of the grid are circumferential lines on the cylindrical balloon wall and helically lines extending from a proximal end to a distal end of the cylindrical balloon wall. The grid lines may be spaced at regular intervals or at irregular intervals. The grid may include two circumferential and two helical lines and thus provide four intersections at which windows are located. The grid may include three circumferential and two helical lines and thus provide six intersections at which windows are located. The grid may include four circumferential and two helical lines and thus provide eight intersections at which windows are located. The grid may include five circumferential and two helical, lines and thus provide ten intersections at which windows are located (as illustrated in FIGS. 11c and 11d). The grid may include two circumferential and three helical lines and thus provide six intersections at which windows are located. The grid may include three circumferential and three helical lines and thus provide nine intersections at which windows are located. The grid may include four circumferential and three helical lines and thus provide twelve intersections at which windows are located. Or the grid may be includes any desired number of circumferential and helical lines in my regular or irregular pattern so long as the windows provide complete circumferential coverage. It can be appreciated that significant circumferential overlap is created by such a grid pattern of windows. As the windows correspond to the sites on the vessel wall where the ablation treatment is provided, such circumferential overlap helps to ensure complete circumferential treatment of a vessel wall.

Multilayer balloons 22 having windows 28 may be made according to one of the methods described herein or by another suitable method. In one method, the first layer 44 and the second layer 46 of the balloon are manufactured separately, using blow-molding techniques or other suitable methods. Holes are formed in second layer 46 by a laser, hole punch, mechanical or hydraulic cutting element or other suitable technique. The first layer 44 is positioned inside of the second layer 46 and the two layers 44, 46 are fused together using heat, a chemical solvent, an adhesive or other suitable technique. In some cases, the two layers may be positioned inside of a mold and/or pressure may be exerted inside layer 44 to fuse the two layers in an expanded position using heat, solvents or adhesives. In some instances, the two layers are not directly joined but rather are separately attached to shaft 34.

In another method of manufacture, the inner layer 44 is formed over a flexible mandrel. The flexible mandrel has a shape like that of inner layer 44 in the expanded position but is made from a material, such as silicon, that does not adhere well to the material of the inner layer 44. The inner layer 44 may be formed over the flexible mandrel by dip coating, spray coating, blow molding or other suitable techniques. A masking material is applied over the inner layer where the one or more windows 28 are desired. The masking material may be fixed to the inner layer using a removable or temporary adhesive. The flexible mandrel, with the inner layer and masking material thereon is then dip coated again using a non-conductive polymer to form outer layer 46. The outer layer is cut at the edges of the masking material and the masking material along with the outer layer material that is on the masking material is removed, thus forming balloon 22. Finally, the flexible mandrel is removed from within balloon 22.

The helical balloons of the FIG. 8 and FIG. 9 embodiments may be formed from a balloon precursor that has two lumens side by side. The first lumen is the balloon lumen and the second lumen fits over shaft 34. This balloon precursor is formed into a dual layer balloon having windows 28 as discussed above. A straight mandrel is then inserted into the second lumen and the balloon precursor is twisted around the straight mandrel to form the first lumen into a helical shape. The second lumen may be inflated and the twisted balloon precursor is heat set into the helical shape. In some variations, the twisted balloon precursor is inserted into a helical mold and heat set in the helical mold to help for the helical balloon shape. The straight mandrel is then removed from the first lumen and the then helical balloon 22 is joined to a shaft.

In use, a renal ablation system such as system 12 is provided. The system may be used with a standard guide catheter such as a 6 French guide catheter. The balloon and in particular the hydrophilic or techophilic material may be hydrated as part of the preparatory steps. Hydration may be effected by soaking the balloon in a saline solution. A one minute, five minute or other suitable soak may be effect. Then the system 12 may be introduced percutaneously as is conventional in the intravascular medical device arts by using a guide catheter and/or a guide wire. For example, a guide wire such as a 0.014" diameter guidewire may be introduced percutaneously through a femoral artery and navigated to a renal artery using standard radiographic techniques. In some embodiments, a delivery sheath 14 may be introduced over the guide wire and the guide wire may be withdrawn, and the system 12 may be then introduced through the delivery sheath. In other embodiments, the system 12 may be introduced over the guidewire, or the system, including a delivery sheath 14 may be introduced over a guidewire. In embodiments involved a delivery sheath 14, the system 12 may be delivered distally from the distal end of the delivery sheath 14 into position, or the delivery sheath may be withdrawn proximally to expose the system 12. A conductive fluid 26 is introduced into the balloon through fluid inlet lumen 40 and fluid inlet 30. The conductive fluid expands the balloon to the desired size. The balloon expansion may be monitored indirectly by monitoring the volume of conductive fluid introduced into the system or may be monitored through radiographic or other conventional means. Optionally, once the balloon is expanded to the desired size, fluid may be circulated within the balloon by continuing to introduced fluid through the fluid inlet 30 while withdrawing fluid from the balloon through the fluid outlet 32. The rate of circulation of the fluid may be between 2 and 20 ml/min, between 3 and 1.5 ml/mm, between 5 and 10 ml/min or other desired rate of circulation. The balloon may be kept at or near a desired pressure such as a pressure of between 1 and 6 atmospheres, between 1.5 and 4 atmospheres, between 2.5 and 3.5 atmospheres or other desired pressure. The electrode 24 is then activated by supplying energy to the electrode. The energy may be supplied at 400-500 Hz and at between 0.5 and 1 amp. The energy is transmitted through the medium of the conductive fluid and through windows 28 to the blood vessel wall to modulate or ablate the tissue. The second layer 46 of the balloon prevents the energy transmission through the balloon wall except at windows 28 (which lack second layer 46). The progress of the treatment may be monitored by monitoring changes in impedance through the electrode. Other measurements such as pressure and/or temperature measurements may be conducted during the procedure as desired. The circulation of the conductive fluid 26 may mitigate the temperature rise of the tissue of the blood vessel 48 in contact with the windows 28. The electrode 24 is preferably activated for an effective length of time, such as 1 minute or 2 minutes. One the procedure is finished at a particular location, the balloon 22 may be partially or wholly deflated and, moved to a different location such as the other renal artery, and the procedure may be repeated at another location as desired using conventional delivery and repositioning techniques.

Examples

While various embodiments of the nerve modulation system have been described with respect to the drawings, several embodiments will now be described using claim language. However, the following examples are not intended to be inclusive of every embodiment or combination of features described herein.

1. An intravascular catheter, comprising:
an elongate member having a proximal end and a distal end:
a balloon having art interior surface, and exterior surface, a lumen defined by the interior surface and comprising at least one section that is permeable to RF radiation, the at least one section extending from the interior surface of the balloon to the exterior surface of the balloon; and
an electrode disposed in the balloon.

2. The intravascular catheter of example 1 wherein the balloon further comprises at least one section that is non-electrically conductive.

3. The intravascular catheter of any of examples 1-2 wherein the balloon comprises three or more sections that are permeable to RF radiation.

4. The intravascular catheter of example 3 wherein the three or more sections are spaced circumferentially and longitudinally with respect to each other.

5. The intravascular catheter of any of examples 3-4 wherein the balloon comprises four sections that are permeable to RF radiation.

6. The intravascular catheter of example 1 wherein the at least one section is a helically shaped section.

7. The intravascular catheter of example 1 wherein the at least one section is a cylindrical section extending around the circumference of the balloon.

8. The intravascular catheter of example 7 wherein the at least one section is situated centrally on the balloon between a proximal end of the balloon and a distal end of the balloon.

9. The intravascular catheter of any of examples 1-2 wherein the balloon has a helically-shaped lumen.

10. The intravascular catheter of example 9 wherein the at least one section is helically shaped and extends along the outer diameter of the balloon, 11. The intravascular system of example 9 wherein the balloon comprises three or more sections that are permeable to RF radiation.

12. The intravascular system of example 11 wherein the three or more sections are spaced circumferentially and longitudinally with respect to each other, 13. The intravascular system of any of examples 11-12 wherein the balloon comprises four sections that are permeable to RF radiation.

14. The intravascular catheter of any of examples 9-13 wherein the sections are located on the outer diameter of the spiral.

15. The intravascular catheter of any of examples 2-14 wherein the at least one RF permeable section comprises a compliant polymeric material.

16. The intravascular catheter of example 15 wherein the non-electrically conductive section comprises a non-compliant polymeric material.

17. The intravascular catheter of any of examples 1-16 wherein the at least one RF permeable section comprises a hydrophilic polymer, 18. The intravascular catheter of example 17 wherein the at least one RF permeable section comprises a hydrophilic polyurethane.

19. The catheter of any of examples 1-18 wherein the at least one RF permeable section comprises a hydrophilic polymer selected from the group consisting of hydrophilic Pebax, hydrophilic nylons, hydrophilic polyesters, or block co-polymers with built-in hydrophilic blocks, Pebax MV 1074, Pebax MV 1041, Pebax MP 1878, Pebax MV-3000, Pebax MB-1657.

20. The catheter of any of examples 17-19 wherein the at least one RF permeable section comprises the hydrophilic polymer blended with a second polymer.

21. The catheter of example 20 wherein the second polymer is selected from a group consisting of Pebax 6333, Pebax 7033, Pebax 7233, Nylon 12, Vestamid L2101F, Grilamid L20, and Grilamid L25.

22. The catheter of any of examples 17-21 wherein the hydrophilic polymer has between 20% to 50% hydrophilicity.

23. The catheter of any of examples 2-22 wherein the non-electrically conductive section comprises a non-hydrophilic polymer.

24. The intravascular catheter of any of examples 2-23 wherein the non-electrically conductive section comprises a non-hydrophilic polyurethane.

25. The intravascular catheter of any of examples 1-24 wherein the balloon comprises a first layer and a second layer.

26. The intravascular catheter of example 25 wherein the first layer is permeable to RF radiation and the second layer is non-electrically conductive.

27. The intravascular catheter of any of examples 25-26 wherein the first layer is inside the second layer.

28. The intravascular catheter of any of examples 25-27 wherein the at least one section that is permeable to RF radiation does not include the second layer.

29. The intravascular catheter of any of examples 25-28 wherein the at least one section that is permeable to RF radiation consists essentially of the first layer.

30. The intravascular catheter of any of examples 25-29 wherein at the at least one section that is permeable to RF radiation, the first layer defines the outer surface of the balloon.

31. The intravascular catheter of example 25 wherein the first layer is permeable to RF radiation and the second layer is non-electrically conductive, wherein the first layer is generally inside the second layer, wherein at the at least one section that is permeable to RF radiation, the first layer defines the outer surface of the balloon, and wherein at the at least one section that is permeable to RF radiation, the first layer extends radically beyond the second layer.

32. The intravascular catheter of example 31 wherein the at least one section that is permeable to RF radiation comprises a plurality of convex windows.

33. The intravascular catheter of any of examples 1-32 wherein the electrode extends under at least one section that is permeable to RF.

34. The intravascular catheter of any of examples 1-32 wherein the electrode extends for at least 80% the length of the balloon, 35. The intravascular catheter of any of examples 1-34 wherein the electrode is helically shaped.

36. The intravascular catheter of any of examples 1-35 wherein the elongate member extends the length of the balloon.

37. The intravascular catheter of example 36 wherein the electrode is disposed on an outer surface of the elongate member.

38. The intravascular catheter of any of examples 36-37 wherein the elongate member comprises a guidewire lumen having an open distal end.

39. The intravascular catheter of any of examples 36-38 wherein the elongate member further comprises a fluid supply lumen having an opening fluidly connected to the balloon lumen.

40. The intravascular catheter of example 39 wherein the elongate member further comprises a fluid return lumen having an opening fluidly connected to the shaft, 41. The intravascular catheter of example 40 wherein the fluid supply lumen opening is distal the fluid return lumen opening.

42. The intravascular catheter of example 41 wherein the fluid supply lumen opening is in a distal waist of the balloon.

43. The intravascular catheter of example 42 wherein the fluid return lumen opening is in a proximal waist of the balloon.

44. The intravascular catheter of any of examples 1-43 further comprising a temperature sensor.

45. The intravascular catheter of example 44 wherein the temperature sensor is disposed on the elongate member.

46. The intravascular catheter of example 44 wherein the temperature sensor is disposed on the balloon.

47. An intravascular catheter, comprising:
an elongate member having a proximal end and a distal end;
a balloon having a lumen and a balloon wall, the balloon wall comprising one or more RF permeable windows through a non-electrically conductive balloon wall, the one ore move RF permeable windows impervious to fluid flow;
an electrode disposed within the balloon and extending distally to the furthest distal RF permeable section.

48. The intravascular catheter of example 47, wherein the electrode is helically shaped.

49. The intravascular catheter of any of examples 47-48 wherein the elongate member extends through the balloon.

50. The intravascular catheter of example 49 further comprising a fluid supply lumen and fluid return lumen fluidly connected to the balloon lumen.

51. An intravascular catheter, comprising:
an elongate member having a proximal end and a distal end;
a balloon having an interior surface, an exterior surface, a lumen defined by the interior surface and a cylindrical wall extending between the interior surface and the exterior surface, the cylindrical wall having a proximal end and a distal end, the balloon having a plurality of electrically conductive windows disposed in the wall and able to pass an electric current between the interior surface and the exterior surface, the plurality of windows arranged such that every line extending along the wall the shortest distance from the proximal end of the wall to the distal end of the wall passes through at least one window, wherein at least one of the plurality of windows extends further in a circumferential direction than in an axial direction and wherein the balloon wall is otherwise electrically insulative; and
an electrode disposed in the balloon.

52. The catheter of example 51 wherein at least one of the plurality of windows is oval.

53. The catheter of example 51 wherein at least one of the plurality of windows is oblong, 54. The catheter of example 51 wherein at least one of the plurality of windows is diamond-shaped.

55. The catheter of example 51 wherein at least one of the plurality of windows is bowtie-shaped.

56. The catheter of any of examples 51-55 wherein the plurality of windows are spaced axially from each other.

57. The catheter of any of examples 51-56 wherein the plurality of windows are arranged in a spiral shape on the balloon wall.

58. The catheter of any of examples 51-57 wherein any two adjacent windows circumferentially overlap such that a line extending along the wall the shortest distance from the proximal end of the wall to the distal end of the wall passes through the two adjacent windows.

59. The catheter of example 58 wherein any two adjacent windows have a circumferential overlap of at least 0.3 mm.

60. The catheter of example 58 wherein any two adjacent windows have a circumferential over lap of at least 0.4 mm.

61. The catheter of example 58 wherein any two adjacent windows have a circumferential overlap of at least 0.5 mm.

62. The catheter of any of examples 58-61 wherein any two adjacent windows have a circumferential overlap of between 20% and 30% of the circumferential dimension of one of the two adjacent windows.

63. The catheter of any of examples 58-62 wherein any two adjacent windows have a circumferential overlap of between 24% and 26% of the circumferential dimension of one of the two adjacent windows, 64. The catheter of any of examples 58-63 wherein any two adjacent windows have a circumferential overlap of between 6% and 7% of a circumferential dimension of the cylindrical balloon wall.

65. The catheter of any of examples 58-63 wherein any two adjacent windows have a circumferential overlap of between 10% and 14% of a circumferential dimension of the cylindrical balloon wall.

66. The catheter of any of examples 51-65 wherein the ratio of the circumferential dimension to the axial dimension of at least, one of the plurality of windows is between 1.5:1 and 4:1.

67. The catheter of any of examples 51-65 wherein the ratio of the circumferential dimension to the axial dimension of at least one of the plurality of windows is 1.5:1.

68. The catheter of any of examples 1-65 wherein the ratio of the circumferential dimension to the axial dimension of at least one of the plurality of windows is about 2:1 and 4:1.

69. The catheter of any of examples 1-65 wherein the ratio of the circumferential dimension to the axial dimension of at least one of the plurality of windows is about 3:1.

70. The catheter of any of examples 1-69 wherein the ratio of the circumferential dimension to the axial dimension is the same for each of the plurality of windows.

71. The catheter of any of examples 1-70 wherein each of the plurality of windows is the same shape.

72. The catheter of any of examples 1-71 wherein the plurality of windows comprises four windows.

73. The catheter of any of examples 1-72 wherein the plurality of windows comprises six windows.

74. The catheter of any of examples 1-73 wherein the plurality of windows comprises eight windows.

75. The catheter of any of examples 1-74 wherein the plurality of balloons are arranged on the intersections of a grid wherein the grid lines are a plurality of circumferential lines of the balloon wall and a plurality of helical lines extending from the proximal end of the balloon wall to the distal end of the balloon wall.

76. The catheter of example 75 wherein the plurality of helical lines are equally spaced around the balloon walls.

77. The catheter of any of examples 75-76 wherein the plurality of helical lines consist of two helical lines.

78. The catheter of any of examples 75-76 wherein the plurality of helical lines consist of three helical lines, 79. The catheter of any of examples 75-76 wherein the plurality of helical lines consist of four helical lines.

80. The catheter of any of examples 75-79 wherein the plurality of circumferential lines are spaced at regular intervals.

81. The catheter of any of examples 75-80 wherein the plurality of circumferential lines consist of two circumferential lines.

82. The catheter of any of examples 75-80 wherein the plurality of circumferential lines consist of three circumferential lines.

83. The catheter of any of examples 75-80 wherein the plurality of circumferential lines consist of four circumferential lines.

84. The catheter of any of examples 51-83 wherein a circumferential dimension of at least one of the plurality of balloons is between 20% and 30% of the circumference of the cylindrical balloon wall.

85. The catheter of any of examples 51-84 wherein a circumferential dimension of at least one of the plurality of balloons is between 22% and 28% of the circumference of the cylindrical balloon wall.

86. The catheter of any of examples 51-85 wherein a circumferential dimension of at least one of the plurality of balloons is between 24% and 26% of the circumference of the cylindrical balloon wall 87. The catheter of any of examples 51-86 wherein the plurality of windows comprises a hydrophilic polymer.

88. The catheter of any of examples 51-87 wherein the plurality of windows comprises a hydrophilic polymer selected from the group consisting of hydrophilic Pebax, hydrophilic nylons, hydrophilic polyesters, or block co-polymers with built-in hydrophilic blocks, Pebax MV1074, Pebax MV 1041, Pebax MP 1878, Pebax MV-3000, Pebax MB-1657.

89. The catheter of any of examples 87-88 wherein the plurality of windows comprises the hydrophilic polymer blended with a second polymer.

90. The catheter of example 89 wherein the second polymer is selected from a group consisting of Pebax 6333, Pebax 7033, Pebax 7233. Nylon 12, Vestamid L2101F, Grilamid L20, and Grilamid L25.

91. The catheter of any of examples 87-90 wherein the hydrophilic polymer has between 20% to 50% hydrophilicity.

92. The catheter of any of examples 51-91 wherein the balloon wall comprises a non-hydrophilic polymer.

93. The catheter of any of examples 51-92 wherein the balloon comprises a first layer and a second layer.

94. The intravascular catheter of example 70 wherein the first layer is electrically conductive and the second layer is non-electrically conductive, 95. The intravascular catheter of any of examples 93-94 wherein the first layer is inside the second layer.

96. The intravascular catheter of any of examples 93-95 wherein plurality of windows do not include the second layer.

97. The intravascular catheter of any of examples 93-96 wherein the plurality of windows consist essentially of the first layer.

98. The intravascular catheter of any of examples 51-97 wherein the electrode extends for at least 50% the length of the balloon.

99. The intravascular catheter of any of examples 51-97 wherein the electrode extends for at least 80% the length of the balloon.

100. The intravascular catheter of any of examples 51-99 wherein the electrode extends for the length of the balloon.

101. The intravascular catheter of any of examples 51-99 wherein the electrode is helically shaped.

102. The intravascular catheter of any of examples 51-101 wherein the elongate member extends the length of the balloon.

103. The intravascular catheter of example 102 wherein the electrode is disposed on an outer surface of the elongate member.

104. The intravascular catheter of any of examples 102-103 wherein the elongate member comprises a guidewire lumen having an open distal end.

105. The intravascular catheter of any of examples 102-104 wherein the elongate member further comprises a fluid supply lumen having an opening fluidly connected to the balloon lumen.

106. The intravascular catheter of example 105 wherein the elongate member further comprises a fluid return lumen having an opening fluidly connected to the shaft.

107. The intra vascular catheter of example 106 wherein the fluid supply lumen opening is distal the fluid return lumen opening.

108. The intravascular catheter of example 107 wherein the fluid supply lumen opening is in a distal waist of the balloon.

109. The intravascular catheter of example 108 wherein the fluid return lumen opening is in a proximal waist of the balloon.

110. The intravascular catheter of any of examples 51-109 further comprising a temperature sensor.

111. The intravascular catheter of example 110 wherein the temperature sensor is disposed on the elongate member.

112. The intravascular catheter of example 110 wherein the temperature sensor is disposed on the balloon.

113. A method of nerve modulation, comprising:
providing a catheter according to any of examples 1-112;
moving the balloon to a region of interest;
inflating the balloon with an electrically conductive fluid; and
activating the electrode.

114. The method of example 113 wherein the step of moving the balloon to a region of interest includes the step of advancing the catheter within a blood vessel.

115. The method of any of examples 113-114 wherein the step of moving the balloon to a region of interest includes the step of advancing the catheter along a guide wire.

116. The method of any of examples 113-115 wherein the step of inflating the balloon includes the step of contacting the outer wall of the balloon to the region of interest.

117. The method of example 116 further comprising the step of circulating the fluid through the balloon at a rate of between 5 ml/min and 10 ml/min.

118. The method of any of examples 114-117 wherein the electrically conductive fluid comprises saline.

119. The method of any of examples 114-118 wherein the electrically conductive fluid comprises a hypertonic solution.

120. The method of any of examples 114-119 wherein the electrically conductive fluid comprises a contrast solution.

121. The method of any of examples 113-120 further comprising the step of hydrating the balloon prior to moving the balloon to a region of interest.

122. The method of example 121 wherein the step of hydrating the balloon comprises the step of soaking the balloon in a saline solution.

123. The method of example 72 wherein the step of soaking the balloon in a saline solution involves soaking of soaking the balloon in a saline solution for at least one minute.

124. The method of example 72 wherein the step of soaking the balloon in a saline solution involves soaking of soaking the balloon in a saline solution for at least five minutes.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. An intraluminal catheter, comprising:
an elongate member having a proximal end, a distal end, and a longitudinal axis;
a balloon at the distal end of the member having a length along the member and a wall that defines an interior of the balloon;
the wall comprising a plurality of sections that are not permeable to RF radiation and at least one window that is permeable to RF radiation; and
an electrode disposed within the balloon interior;
wherein the at least one window is arranged so that any line drawn along the length of the balloon parallel to the longitudinal axis of the member passes through the at least one window;
wherein the wall comprises a first layer that is permeable to RF radiation and a second layer that is non-electrically conductive;
wherein the at least one window is formed in the wall by the absence of the second layer; and
wherein the at least one window lies along a helical path that wraps around a circumference of the balloon at least one full turn.

2. The catheter of claim 1, wherein the helical path wraps around the circumference of the balloon a plurality of full turns.

3. The catheter of claim 1, comprising two of more helical paths wrapped in parallel paths around the circumference of the balloon at least one full turn.

4. The catheter of claim 1, wherein the window arrangement comprises a plurality of windows arranged so that any line drawn along the length of the balloon parallel to the longitudinal axis of the member passes through one or more of the windows.

5. The catheter of claim 1, wherein the window arrangement comprises a single window arranged along the helical path so that any line drawn along the length of the balloon parallel to the longitudinal axis of the member passes through the single window one or more times.

6. The catheter of claim 5, wherein the single window is arranged along the entire helical path.

7. An intraluminal catheter, comprising:
an elongate member having a proximal end, a distal end, and a longitudinal axis;
a balloon at the distal end of the member having a length along the member and a wall that defines an interior of the balloon;
the wall comprising a plurality of sections that are not permeable to RF radiation and a plurality of windows that are permeable to RF radiation; and
an electrode disposed within the balloon interior;
wherein the windows are arranged so that any line drawn along the length of the balloon parallel to the longitudinal axis of the member passes through at least one of the windows;
wherein the balloon comprises a first layer that is permeable to RF radiation and a second layer that is non-electrically conductive;
wherein the windows do not include the second layer; and
wherein the windows have a length dimension that is larger than a width dimension and the length dimension is oriented with respect to the longitudinal axis of the member.

8. The catheter of claim 7, wherein the length dimension is oriented parallel, perpendicular, or an approximate 45-degree angle, to the to the longitudinal axis of the member.

9. The catheter of claim 8, wherein the windows have shapes on forms of ovals, rectangles, diamonds or bowties.

10. The catheter of claim 7, wherein the windows are arranged so that any line drawn along the length of the balloon parallel to the longitudinal axis of the member passes through two or more windows.

11. An intraluminal catheter, comprising:
an elongate member having a proximal end, a distal end, and a longitudinal axis;
a balloon at the distal end of the member having a length along the member and a wall that defines an interior of the balloon;
the wall comprising a plurality of sections that are not permeable to RF radiation and a plurality of windows that are permeable to RF radiation; and
an electrode disposed within the balloon interior;
wherein the windows are arranged so that any line drawn along the length of the balloon parallel to the longitudinal axis of the member passes through at least one of the windows;
wherein the wall comprises a first layer that is permeable to RF radiation and a second layer that is non-electrically conductive;
wherein the at least one window is formed in the wall by the absence of the second layer; and
wherein the windows are arranged in a grid pattern along circumferential lines perpendicular to the longitudinal axis of the member and helical lines at an angle to the longitudinal axis.

12. The catheter of claim 11, wherein the windows are arranged at intersections of the circumferential lines and the helical lines.

13. The catheter of claim 11, wherein at least some of the windows are arranged in the grid pattern at regular intervals along the circumferential lines or the helical lines.

14. The catheter of claim 11, wherein the windows are arranged in the grid pattern at irregular intervals along the circumferential lines or the helical lines.

15. The catheter of claim 11, wherein the windows are arranged in the grid pattern at regular intervals along both the circumferential lines and the helical lines.

16. The catheter of claim 11, wherein the helical lines in the grid pattern are at an approximate 45-degree angle to the longitudinal axis.

17. The catheter of claim 11, wherein any line drawn along the length of the balloon parallel to the longitudinal axis of the member passes through two or more windows.

18. The catheter of claim 11, wherein any line drawn along the length of the balloon parallel to the longitudinal axis of the member passes through at least two windows in adjacent circumferential lines or helical lines of the grid pattern.

* * * * *